United States Patent [19]
Chandrasekhar et al.

[11] Patent Number: 4,851,088
[45] Date of Patent: Jul. 25, 1989

[54] ELECTROCHEMICAL DETECTION OF CARBON DIOXIDE

[75] Inventors: Prasanna Chandrasekhar, Horsham, Pa.; H. V. Venkatasetty, Burnsville, Minn.

[73] Assignee: Honeywell Inc., Minneapolis, Minn.

[21] Appl. No.: 21,956

[22] Filed: Mar. 5, 1987

[51] Int. Cl.$^4$ .............................. G01N 27/46
[52] U.S. Cl. .................... 204/1 T; 204/412; 204/414; 204/415
[58] Field of Search ............ 204/1 P, 1 T, 414, 415, 204/412

[56] References Cited

U.S. PATENT DOCUMENTS

| | | | |
|---|---|---|---|
| 3,575,836 | 4/1971 | Sternberg | 204/415 |
| 3,718,563 | 2/1973 | Krull et al. | 204/415 |
| 3,833,495 | 9/1974 | Grubb | 204/414 |
| 3,838,080 | 4/1975 | Luck | 204/415 |
| 4,169,779 | 10/1979 | Tataria et al. | 204/415 |
| 4,521,290 | 6/1985 | Venkatasetty | 204/415 |
| 4,522,690 | 6/1985 | Venkatasetty | 204/415 |
| 4,571,292 | 2/1986 | Liu et al. | 204/415 |
| 4,655,880 | 4/1987 | Liu | 204/403 |
| 4,662,996 | 5/1987 | Venkatasetty | 204/415 |

Primary Examiner—T. Tung
Attorney, Agent, or Firm—C. G. Mersereau

[57] ABSTRACT

An electrochemical system for the detection of carbon dioxide includes a single cell chamber exposed to the sample medium through a polymeric barrier membrane, a single set of electrodes and utilizes an aprotic non-aqueous, gelled solvent/electrolyte medium which allows measurement of $CO_2$ in the presence of both oxygen and water vapor.

25 Claims, 2 Drawing Sheets

ELECTROCHEMICAL DETECTION OF CARBON DIOXIDE

BACKGROUND OF THE INVENTION

1. Field of the Invention

The present invention relates generally to the electrochemical measurement of the concentration of a species of interest and, more particularly, to the electrochemical measurement of carbon dioxide ($CO_2$) in a liquid or gaseous fluid which may contain both oxygen and water vapor.

2. Description of the Prior Art

Electrochemical reactions based on oxidation or reduction of metals and compounds at an electrode are highly selective because of the characteristic redox potential at which oxidation or reduction of the electroactive species occurs. Selection of the electrode material in combination with an electrolyte solution system has become very important in determining sensitivity and selectivity. This is especially important in situations where one species is sought to be determined quantitatively in the presence of other species which may exhibit similar reactions.

Carbon dioxide formerly was quantitatively detected by electrochemical means wherein the concentration of $CO_2$ in air or other vapor mixtures was measured by reduction at a stationary electrode in an environment from which oxygen had been previously eliminated. Air, in which carbon dioxide is most frequently measured, normally contains both oxygen and water vapor. The reduction potentials of both oxygen and water vapor are lower than that of carbon dioxide. It was, therefore, necessary to eliminate these interfering components from the sample gas to prevent erroneous readings. This could be a complicated procedure.

More recently, a system has been proposed in which carbon dioxide may be measured quantitatively in the presence of oxygen. Such a system is disclosed in U.S. Pat. No. 4,377,466 issued to W. J. Albery. That system employs a dual electrochemical cell structure having first and second cells separated by a $CO_2$ permeable membrane which are designed to be sequentially encountered by the sample gas. Both cells contain working, reference and counter electrodes. The first cell contains an aqueous electrolyte system and the second, a non-aqueous solvent/electrolyte system. The potentials of the first and second working electrodes are held constant with respect to the first and second reference electrodes respectively.

The first cell is energized with a potential sufficient to reduce any oxygen molecules in the sample but, not carbon dioxide molecules. The carbon dioxide molecules pass unaffected through the $CO_2$ permeable membrane separating the cells. The second, non-aqueous cell is maintained at a potential level which is high enough to reduce carbon dioxide.

The circuit of the system is so configured that the current in the first cell is basically proportional to the concentration of the species reduced in the first cell and that of the second cell likewise proportional to the species reduced in that cell. This enables the determination of the concentration of both oxygen and carbon dioxide in a sample gas stream assuming that there are no interfering species.

While the system of Albery or similar systems represent a clear advance over earlier electrochemical systems for the detection of carbon dioxide, they do suffer from certain significant drawbacks which can lead to inaccuracies in results. First, inaccuracies may result, especially at low concentrations of carbon dioxide, with respect to the aqueous first cell inasmuch as a certain amount of the carbon dioxide will dissolve in the aqueous solution according to the equilibrium equation $H_2O + CO_2 = HCO_3^- + H^+$. It is also possible that the carbon dioxide may react to some extent with one or more other species in the aqueous solution.

In addition, interference brought about by the presence of water or water vapor in the cell environment is not eliminated. It is well documented in the literature that water present in non-aqueous solvents is reduced at about $-1.5$ v and beyond and therefore can be a serious interferent in $CO_2$ detection. Dimethyl sulfoxide (DMSO), for example, disclosed in Albery, cited above, is not stable in the presence of water.

Furthermore, aqueous electrolyte solutions are subject to solvent loss by evaporation especially at higher temperatures. This, of course, reduces the temperature range over which such a cell may be operated successfully for any length of time.

SUMMARY OF THE INVENTION

The present invention solves many of the problems encountered by prior art electrochemical carbon dioxide sensors by providing a single chamber electrochemical cell having a single set of electrodes which allow carbon dioxide detection in the presence of both oxygen and water vapor. The cell of the present invention includes an enclosure or closed hollow chamber with an opening or access covered by a thin non-porous transport polymer barrier membrane of one or more layers that allows permeation of $CO_2$, $O_2$ and a minimum amount of water vapor. The chamber contains but a single set of electrodes including sensing, counter and working electrodes in a non-aqueous gelled electrolyte consisting of a mixed aprotic solvent system and an electrolyte salt in a matrix of gelling agent.

The cell of the invention further contemplates detection of $CO_2$ in both gas phase and dissolved liquid, normally aqueous, phase systems. Aqueous systems may include saline or blood. The gas phase cell normally employs a microporous PTFE separation or transport membrane of a thickness determined by considerations of sensitivity response time and useful life. While single layer membranes can be used for some applications, liquid phase applications normally employ multiple membrane layers which may be of the same or diverse compositions.

The sensing and counter electrodes are preferably of gold and the reference electrode either platinum or gold, preferably platinum. The solvent mixture selected preferably includes the combination of a high donor number solvent such as dimethyl formamide (DMF) and a moderate donor number solvent such as propylene carbonate or $\gamma$-butyrolactone together with a gelling agent such as polyethylene oxide (PEO). The preferred salts are tetraalkylammonium salts such as tetraethylammonium perchlorate and tetraethylammonium hexafluoro phosphate dissolved in the solvent mixture to give a solution (0.2 to 0.5M). Also, a single solvent based electrolyte solution can be used in place of the mixed solvent electrolyte solution.

In operation, the cell is preferably subjected to a potential scan or time variable potential differential between the sensing or working electrode and the reference electrode in lieu of a constant applied potential and the current produced in the cell is monitored. The current output assignable to the reduction of $O_2$ and $H_2O$ vapor impinging on the sensing or working electrode and the current attributed to the reduction of $CO_2$ also impinging on the working electrode are readily differentiable with background subtraction as they manifest themselves at diverse potentials correlated to the potential scan. Of course, where desired, such as in the determination of blood gas samples, $O_2$ can readily be detected with respect to its reduction in the same vein. The applied potential may be linearly ramped but is preferably, multiple potential steps or in the form of a modulated square wave.

DESCRIPTION OF THE PREFERRED EMBODIMENT

The invention contemplates a single chamber for $CO_2$ detection with respect to both wet and dry sampling. Access of the sample to the cell of the invention is controlled by a transport or barrier membrane system. The cell requires but one set of metalized electrodes. The sensor is subjected to a potential scan, in lieu of a constant applied potential, and the current produced at the sensing electrode is monitored. The current assignable to $O_2$, which also may thereby be measured, and water vapor impinging on the sensing electrode and the current assignable to $CO_2$ impinging on the sensing electrode are differentiable with background subtraction because they appear at different potentials during the potential scan. In this manner, unlike the case with prior art systems, the need for an additional set of electrodes for the specific purpose of $O_2$ and water vapor removal from the impinging gas stream or solution is eliminated.

Figure 1A:
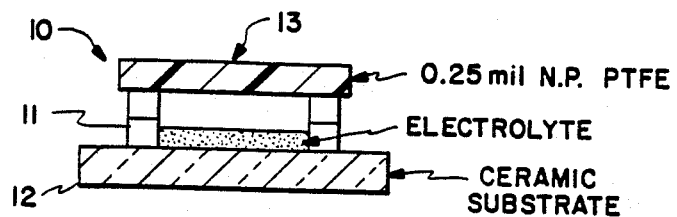
FIGS. 1A, 1B and 1C depict typical schematic cross sections of the sensor cell embodiments usable in the invention.
Figure 1B:
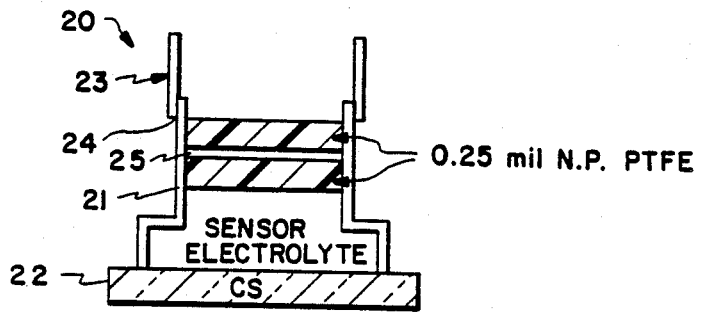
Figure 1C:
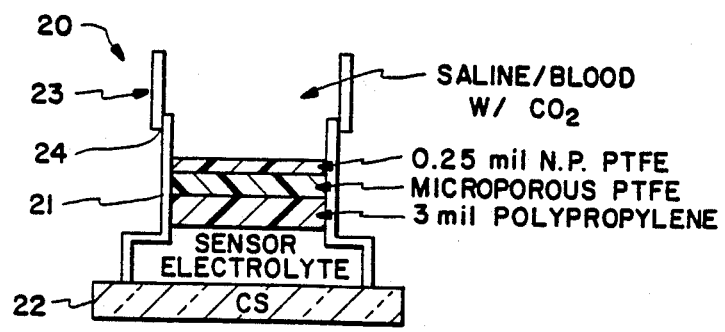

Sections of several of the many possible embodiments of the single cell sensor of the present invention are illustrated in simplified form in FIGS. 1A–1C. The cell shown generally at 10 in FIG. 1A, has sealed sidewalls 11 and a ceramic bottom or substrate member 12. The single barrier or transport membrane is represented by 13.

Likewise FIGS. 1B and 1C depict similar cells 20 having sealed sidewalls 21 and ceramic bottom members 22. The cells of FIGS. 1B and 1C further include extensions or tube members 23 for containing liquid samples such as saline or blood and which may removably attach to the sidewall of the cell as at 24, or are in the form of extensions thereof. These embodiments employ two or three layers of covering membrane material separating the external environment from the cell itself.

Figure 2A:
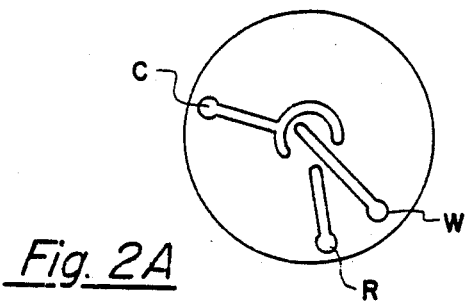
FIGS. 2A, 2B and 2C depict typical electrode configurations for use with cells as in FIG. 1A–1C.
Figure 2B:
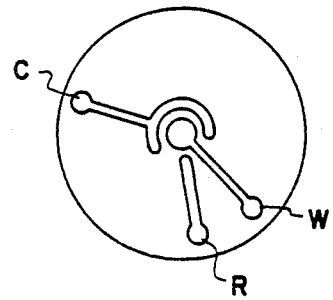
Figure 2C:
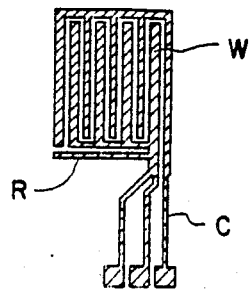

The electrodes illustrated in FIGS. 2A–2C, are shown preferably mounted evaporated or deposited on a ceramic substrate or base as in FIGS. 2A and 2B. These consist of the concentric electrodes systems of FIGS. 2A and 2B and the interdigitated system of FIG. 2C. For most versions, a ceramic cell bottom, base or substrate 12, 22 is now preferred due to the very good electrode adhesion and durability of these substrates in comparison to materials such as polyethelene and polypropylene, employed and evaluated in earlier embodiments. These latter materials may suffice for certain applications, however.

The cell also contains an amount of a gelled nonaqueous electrolyte which may be in the form of a thin film covering the electrodes in accordance with the invention. The components will now be discussed in greater detail.

The transport or barrier membrane, be it one or several layers, should be one which adequately prevents unwanted foreign matter from penetrating the cell and interfering with its normal operation; but it also must be one which affords sufficient permeability to the ambient atmosphere being tested such that gaseous species and particularly the species of interest, be it $CO_2$ or $O_2$, is readily transported through it. Like the components in the cell of the present invention, it must also be chemically inert to other species in the cell environment and those in the atmosphere being tested. Such materials as polytetrafluoroethylene (PTFE), low density polyethylene, and polypropylene afford excellent properties. In the case of PTFE, although both are transported, the relative permeability or transport of $CO_2$ over $O_2$, for example, is about 3.

The membrane materials and layer configurations shown in FIGS. 1A–1C are meant to be illustrative, only, and other configurations and materials can be substituted as the particular application demands. To maximize response time where such is critical such as in future space station applications or the like, a single microporous (3 $\mu$m poresize) PTFE membrane such as Gortex (Trademark of W. L. Gore Associates, Elkton, MD) can be employed. That membrane can be made extremely thin for a porous membrane, e.g. 1.4 mil, to enable an extremely high sensitivity and a quick response time.

For a relatively long life $CO_2$ sensor suitable for indoor air quality and commecial applications, a single 0.25 mil, non-porous (N.P.), gas-permeable PTFE membrane, such as that shown in FIG. 1A, which is available commercially (as from CHEMFAB, West Palm Beach, Fla.) has produced very good results. The nonporous PTFE membrane ensures a longer lifetime for the sensor, although it reduces the sensivity and increases the response time by a factor of 2 to 3 in comparison to the microporous Gortex membrane cell. This, however, is of little consequence, except in applications such as the space station, above, where detection time is of the essence.

In a liquid phase $CO_2$ or $CO_2/O_2$ sensor, which has potential medical applications, such as in blood-gas analysis, one encapsulating barrier transport membrane which produces very successful results in a doublemembrane consisting of two 0.25 mil nonporous, gaspermeable teflon membranes with a small (approximately 1 mil. or less) air gap 25 between them as shown in FIG. 1B. The dual membrane construction ensures that if there are minute deficiencies or pinholes in the membrane material, leakage of the aqueous phase into the sensor does not occur since the likelihood of pinholes of two membranes coinciding is small.

Figure 3A:
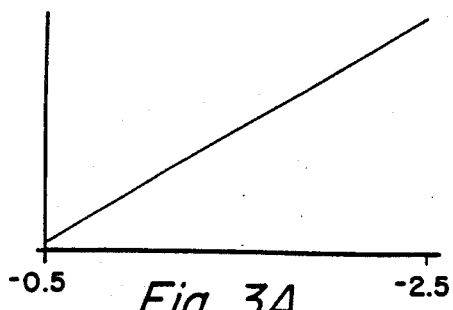
FIGS. 3A, 3C and 3E depict potential scan modes.
Figure 3B:
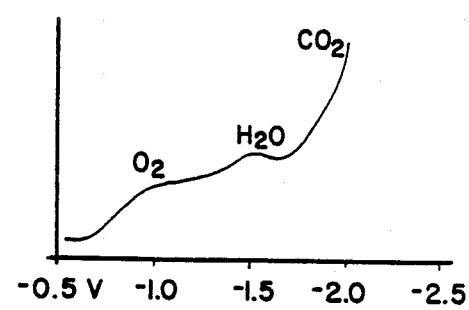
FIGS. 3B, 3D and 3F show typical corresponding cell responses.
Figure 3C:
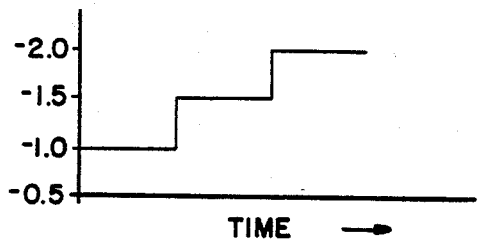

A three membrane version such as that illustrated in FIG. 3C is also suitable for liquid or aqueous phase monitoring. This further illustrates the many possible combinations of membranes contemplated by the invention which may adapt the cell for any specialized application.

The electrodes themselves are illustrated in FIGS. 2A-2C. The electrodes may be in concentric form as shown in FIGS. 2A and 2B or in a interdigital configuration as depicted in FIG. 2C. Both are preferably 2-dimensional and deposited on the ceramic; however, 3-dimensional wire electrodes may also be used. A variety of customary electrode materials function in the cell; but in the preferred embodiment the working and counter electrodes consist substantially of a thin layer of deposited gold and the reference electrode a thin layer of deposited platinum. The electrode substrate may be any suitable high density ceramic material, which the electrodes may readily be deposited and to which they will adhere. The thickness should be sufficient to provide structural support in accordance with the application.

The electrolyte utilized in the cell of the present invention consists of a mixed aprotic solvent system combined with an appropriate electrolyte salt in a gelled matrix which provides sufficient transport for the species of interest and conductance with respect to the electrodes. The preferred solvent mixture includes a solvent selected from a high donor number family together with one selected from those of moderate donor number to provide optimum solvation of the carbon dioxide in the sample gas to be sensed.

Viewing the properties of solvents in terms of donor and acceptor characteristics with reference to empirical or experimentally determined parameters has become an accepted method of characterizing solvation properties. See, for example, Gutmann, Viktor, *The Donor-Acceptor Approaach to Molecular Interactions*, New York (1979). The donor number (DN) has been defined as the molar enthalpy value ($\Delta H$) for the reaction of the donor (D) with $SbCl_5$ as a reference acceptor in a $10^{-3}M$ solution of dichloroethane. According to the reaction:

$$D + SbCl_5 = D\ SbCl_5\ (-H_{D\ SbCl_5} - DN)$$

a partial list of donor numbers for various solvents obtained in accordance with the above equation appears in Table 1.

TABLE 1

| Donor Numbers (DN) for Various Solvents Obtained From Calorimetric Measurements in $10^{-3}$ M Solutions of Dichloroethane with $SbCl_5$ as a Reference Acceptor | |
|---|---|
| Solvent | DN |
| 1,2-Dichloroethane (DCE) | — |
| Benzene | 0.1 |
| Thionyl chloride | 0.4 |
| Acetyl chloride | 0.7 |
| Tetrachloroethylene carbonate (TCEC) | 0.8 |
| Benzoyl fluoride (BF) | 2.3 |
| Benzoyl chloride | 2.3 |
| Nitromethane (NM) | 2.7 |
| Nitrobenzene (NB) | 4.4 |
| Acetic anhydride | 10.5 |
| Phosphorus oxychloride | 11.7 |
| Benzonitrile (BN) | 11.9 |
| Selenium oxychloride | 12.2 |
| Acetonitrile | 14.1 |
| Tetramethylenesulfone (TMS) | 14.8 |
| Dioxane | 14.8 |
| γ-butyrolactone | 15.0 |
| Propylene carbonate | 15.0 |

TABLE 1-continued

| Donor Numbers (DN) for Various Solvents Obtained From Calorimetric Measurements in $10^{-3}$ M Solutions of Dichloroethane with $SbCl_5$ as a Reference Acceptor | |
|---|---|
| Solvent | DN |
| Propandiol-(1,2)-carbonate (PDC) | 15.1 |
| Benzyl cyanide | 15.1 |
| Ethylene sulphite (ES) | 15.3 |
| iso-Butyronitrile | 15.4 |
| Propionitrile | 16.1 |
| Ethylene carbonate (EC) | 16.4 |
| Phenylphosphonic difluoride | 16.4 |
| Methyl acetate | 16.5 |
| n-Butyronitrile | 16.6 |
| Acetone (AC) | 17.0 |
| Ethylacetate | 17.1 |
| Water | 18.0 |
| Phenylphosphoric dichloride | 18.5 |
| Diethyl ether | 19.2 |
| Tetrahydrofuran (THF) | 20.0 |
| Diphenylphosphoric chloride | 22.4 |
| Trimethyl phosphate (TMP) | 23.0 |
| Tributyl phosphate (TBP) | 23.7 |
| Dimethyl formamide (DMF) | 26.6 |
| N—Methyl pyrolidinone (NMP) | 27.3 |
| N—Dimethyl acetamide (DMA) | 27.8 |
| Dimethyl sulfoxide (DMSO) | 29.8 |
| N—Diethyl formamide (DEF) | 30.9 |
| N—Diethyl acetamide (DEA) | 32.2 |
| Pyridine (PY) | 33.1 |
| Hexamethylphosphoric triamide (HMPA) | 38.8 |

In accordance with the present invention it has been found that solvent mixtures including at least one solvent of high donor number, i.e., about 25 or above, provides better solvating properties for $CO_2$. This allows the $CO_2$ to readily pass through the solution unaltered such that it remains an identifiable species to be detected properly at the electrode system as explained below.

This can be blended with a solvent of moderate donor number such as propylene carbonate or γ-butyrolactone. The addition of the solvent having the moderate donor number imparts good electrochemical properties of the solution. The electrolyte salt is preferably a tetraalkylammonium salt such as tetraethyl ammonium perchlorate $(C_2H_5)_4NClO_4$ or tetrabutyl ammonium perchlorate $(C_4H_9)_4NClO_4$. The mixed solvents are combined with the electrolyte salt and the resulting combination is gelled in a matrix of an inert gelling agent such as polyethylene oxide (PEO).

Successful single chamber cells have been operated utilizing a gelled mixed solvent electrolyte system according to compositions which included ten to 20 percent (10-20%) by volume of high donor number solvent DMF (26.6) in combination with a moderate donor number solvent such as propylene carbonate or γ-butyrolactone (15.0) making up the remaining portion of the solvent volume. Polyethylene oxide (molecular weight 100,000) gelling agent was used in quantities of eight to fifteen percent (8-15%) by weight and an amount of tetraethyl ammonium perchlorate electrolyte salt was added.

Figure 4:
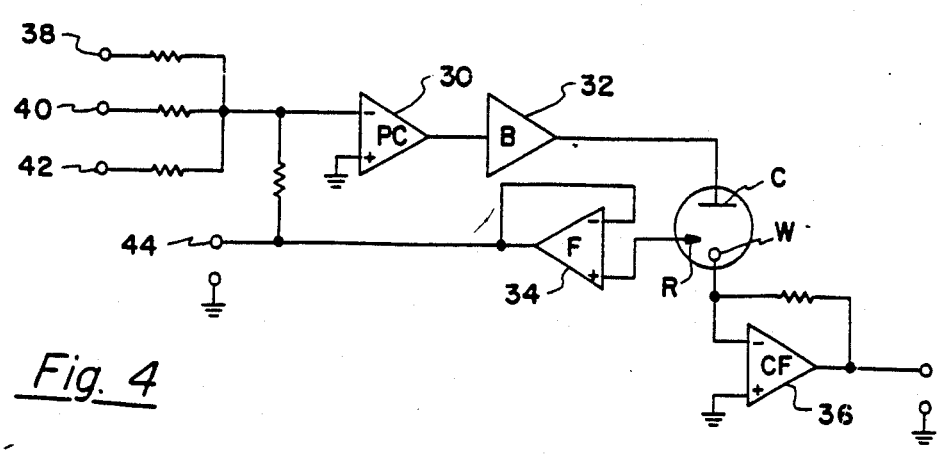
FIG. 4 is a schematic circuit diagram of a typical circuit for operating cell of FIG. 1.

FIG. 4 depicts a schematic circuit diagram of a circuit design in common use which may be used to operate the carbon dioxide detecting electrochemical cell of the invention. It involves working, counter and reference electrodes, respectively, W, C and R as shown. The circuit also contains an operational amplifier 30 with booster amplifier 32 in the output loop. The booster 32 is a noninverting amplifier of low gain capable of delivering higher currents or voltages, or both, than the operational amplifier 30. Since it is noninverting, it can be considered as an extension of amplifier 30. A voltage follower 34 prevents the reference electrode from being loaded by the current fed to the summing point. The working electrode feeds a current follower 36 whose output is proportional to generated cell current, the current follower allows the working electrode to remain at virtual ground which is important for the operation of the system. External potentials may be connected at 38, 40, and 42 and monitored at 44. Cell current may be monitored at the output of 36. The circuit of FIG. 4 also functions to control the potential of working electrode W with respect to reference electrode R.

As shown in FIGS. 3A–3C and 3E, the cell can be interrogated in a variety of modes. FIG. 3A illustrates the application of a constantly increasing or "ramping" function. In this mode the potential between the working electrode W and the reference electrode R is increased through the reduction values at a constant rate.

In FIG. 3C, a step change function for the detection of $O_2$, $H_2O$ and $CO_2$ is illustrated in which the cell is maintained at a first fixed potential difference between the working electrode W and the reference electrode R which is approximately $-1.0V$. This is sufficient to reduce oxygen. Water vapor is then reduced at about $-1.5V$ which also is insufficient to affect the $CO_2$. The fixed potential is thereafter raised to about 2.0V in order to effect reduction and enable detection of $CO_2$. Of course, a separate $O_2$ reading can be made if desired. Similarly, FIG. 3A depicts a ramping mode and FIG. 3E utilizes a "squarewave" waveform in a stepping mode of addressing the cell on a time variable basis.

Figure 3D:
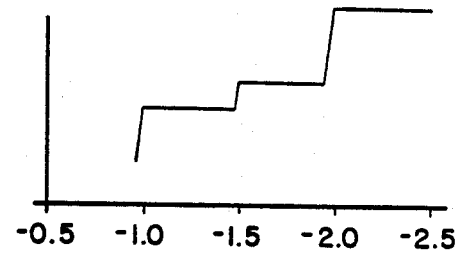
Figure 3E:
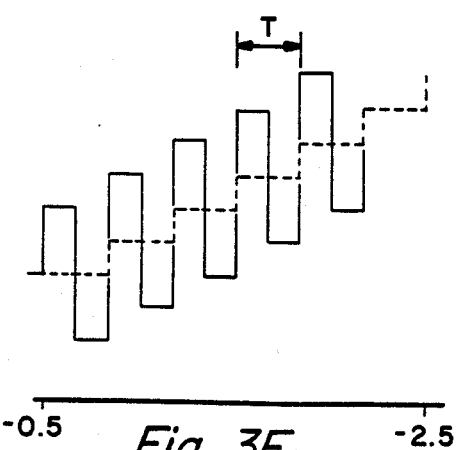
Figure 3F:
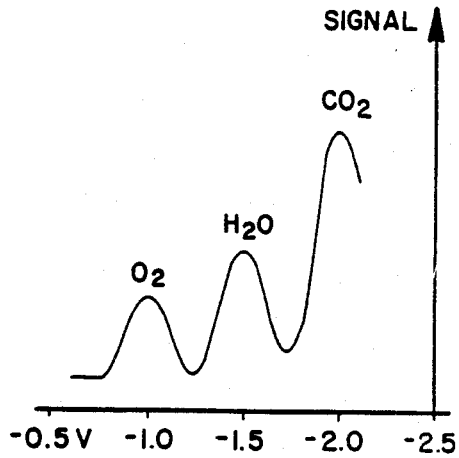

FIGS. 3B, 3D and 3F, illustrate the corresponding output signals which are indicative of the concentration of the constituents measured. The "background" or measurement not due to $CO_2$ may be subtracted from the measurement of $CO_2$ reduction potential to obtain the net value. In applications where the $O_2$ value itself may also separately be of interest, it can also be measured by differentiation from respective background measurements. This may be especially useful in measurements having to do with blood gas analysis, for example.

From the data accumulated, as can be seen in FIGS. 3B, 3D and 3F, the squarewave ramping of FIG. 3F appears to yield more distinct results than the ramping of FIG. 3B. In practical applications, with the system of the present invention, it is readily possible to quantitatively measure concentrations of $CO_2$ as low as about 500 PPM. Although higher concentrations can be detected, the cell is especially useful in detecting concentrations from about 500 PPM to 3000 PPM. Even at these low concentrations, response is quite rapid, in the order of about 15 to 30 seconds.

It can readily be seen that the present invention provides a simplified, single-chamber apparatus for detecting $CO_2$ in the presence of the most common reactive contaminants, i.e., oxygen and water vapor. The gelled electrolyte system associated with the cell makes it easy to package the cell, establishes good contact with the electrodes while, at the same time, prolonging cell life and greatly increasing the operating temperature range of the cell by reducing solvent loss due to evaporation.

What is claimed is:

1. An electrochemical cell for detecting the presence of at least one member of a class of species consisting of $CO_2$, $O_2$, and $H_2O$ as the species of interest in a liquid or gaseous sample mixture which may contain $CO_2$, $O_2$ and $H_2O$ comprising:

a hollow chamber having an opening therein in communication with the sample which may contain the species of interest;

a barrier membrane of polymeric material impervious to liquids but permeable to $CO_2$, $O_2$ and $H_2O$ vapor covering said opening and comprising at least one layer;

a substrate member disposed beneath said barrier of polymeric material;

a set of electrodes including reference, working and counter electrodes disposed on or supported from said substrate member;

a non-aqueous, aprotic, gelled electrolyte system permeable to $CO_2$, $O_2$ and $H_2O$ in contact with said electrodes and further comprising a solvent mixture consisting of a high donor number solvent and a moderate donor number solvent, an amount of electrolyte salt and a compatible gelling agent; and circuit means configured to apply desired potential differences between the working electrode and the reference electrode, said circuit means further including potential control means to modulate said desired potential differences on a time variable basis and including means to measure cell output based on the reduction of $O_2$, $H_2O$ and $CO_2$.

2. The apparatus of claim 1 wherein said potential control means modulates said potential differences in a ramped squarewave form.

3. The apparatus of claim 1 wherein said potential control means modulates said potential differences on a straight line ramp basis.

4. The apparatus of claim 1 wherein said potential control means modulates said potential differences as a step function.

5. The apparatus of claim 1 wherein said barrier membrane comprises a plurality of separate members wherein each of said plurality of separate members is one selected from the group consisting of porous PTFE, non-porous, gas permeable PTFE, low density polyethylene and poly-propylene.

6. The apparatus of claim 5 wherein said barrier membrane comprises a pair of spaced non-porous, gas-permeable PTFE membrane members.

7. The apparatus of claim 1 wherein said barrier membrane consists essentially of a single porous layer of PTFE having a pore size of approximately 3 microns.

8. The apparatus of claim 1 wherein said barrier membrane consists essentially of a single layer of non-porous, gas permeable PTFE having a nominal thickness of less than 0.25 mil.

9. The apparatus of claim 1 wherein said high donor electrolyte solvent in said solvent mixture is DMF and said solvent of moderate donor number is one selected from the group consisting of propylene carbonate and $\gamma$-butyrolactone.

10. The apparatus of claim 9 wherein said electrolyte salt is a tetraalkylammonium salt selected from the group consisting of $(C_2H_5)_4NClO_4$ and $(C_4H_9)_4NClO_4$ and $(C_2H_5)_4NBF_6$.

11. The apparatus of claim 1 wherein said working and counter electrodes are gold and wherein said reference electrode is a material selected from the group consisting of gold and platinum.

12. An electrochemical cell for detecting the presence of one or both of $CO_2$ and $O_2$ in a liquid sample mixture which may contain $CO_2$, $O_2$ and $H_2O$ comprising;
- a hollow chamber having an opening therein in communication with the sample which may contain the species of interest;
- a barrier membrane of polymeric material impervious to liquids but permeable to $CO_2$ and $O_2$ covering said opening and comprising a plurality of separate spaced members;
- means for containing a liquid sample external to said chamber and in contact with said barrier membrane;
- a substrate member disposed beneath said barrier of polymeric material;
- a single set of electrodes including reference, working and counter electrodes disposed on or supported from said substrate member;
- a non-aqueous, aprotic, gelled electrolyte system permeable to $CO_2$ and $O_2$ in contact with said electrodes and further comprising a solvent mixture consisting of a high donor number solvent and a moderate donor number solvent, an amount of electrolyte salt and a compatible gelling agent; and
- circuit means configured to apply desired potential differences between the working electrode and the reference electrode, said circuit means further including potential control means to modulate said desired potential differences on a time variable basis, and including means to measure cell output based on the reduction of $O_2$ and $CO_2$.

13. The apparatus of claim 12 wherein said potential control means modulates said potential differences in a ramped squarewave form.

14. The apparatus of claim 12 wherein said potential control means modulates said potential differences on a straight line ramp basis.

15. The apparatus of claim 12 wherein said potential control means modulates said potential differences as a step function.

16. The apparatus of claim 12 wherein said high donor electrolyte solvent in said solvent mixture is DMF and said solvent of moderate donor number is one selected from the group consisting of propylene carbonate and $\gamma$-butyrolactone, said electrolyte salt is a tetraalkylammonium salt selected from the group consisting of $(C_2H_5)_4NClO_4$ and $(C_4H_9)_4NClO_4$ and $(C_2H_5)_4NBF_6$, and wherein said gelling agent is polyethylene oxide.

17. The apparatus of claim 16 wherein each of said plurality of separate spaced members is one selected from the group consisting of porous PTFE, non-porous, gas permeable PTFE, low density polyethylene and poly-propylene.

18. The apparatus of claim 17 wherein said working and counter electrodes are gold and wherein said reference electrode is of a material selected from the group consisting of gold and platinum.

19. The apparatus of claim 16 wherein said working and counter electrodes are gold and wherein said reference electrode is of a material selected from the group consisting of gold and platinum.

20. A method for detecting the presence of at least one species of interest of a class consisting of $CO_2$, $O_2$ and $H_2O$ in a liquid or gaseous sample mixture containing at least one other of said species comprising the steps of:
- causing the species of said class contained in the sample to be transported across from an outer surface to an inner surface of a barrier membrane impervious to liquids but permeable to $CO_2$, $O_2$ and $H_2O$ vapor, into a cell means, said cell means comprising, a set of electrodes including reference, working and counter electrodes disposed beneath said barrier, a non-aqueous, aprotic, gelled electrolyte system permeable to $CO_2$, $O_2$ and $H_2O$ in contact with said electrodes and further comprising a solvent mixture consisting of a high donor number solvent and a moderate donor number solvent, and an amount of electrolyte salt and a compatible gelling agent;
- determining the presence of each of said species of interest by applying a time variable potential difference between the working electrode and the reference electrode which sequentially applies sufficient potential to reduce each such species of interest in increasing order; and
- measuring cell output based on the reduction of each of $O_2$, $H_2O$ and $CO_2$.

21. The method of claim 20 wherein said potential difference is modulated in a ramped squarewave form.

22. The method of claim 20 wherein said potential difference is modulated on a straight line ramp basis.

23. The method of claim 20 wherein potential difference in modulated as a step function with respect to the reduction potentials of $O_2$, $H_2O$ and $CO_2$.

24. An electrochemical cell for detecting the presence of at least one member of a class of species of interest in a liquid or gaseous sample mixture which may contain one or more of such species of interest said class consisting of plurality of gaseous species each having a distinct oxidation or reduction potential within the operating range of the potential of said cell comprising:
- a hollow chamber having an opening therein in communication with the sample which may contain the species of interest;
- a barrier membrane of polymeric material impervious to liquids but permeable to the species of interest in gaseous form covering said opening and comprising at least one layer;
- a set of three electrodes including reference, working and counter electrodes disposed beneath said barrier membrane and in predetermined spaced relation thereto and to each other;
- a non-aqueous, aprotic, gelled electrolyte system permeable to the species of interest in contact with said electrodes and further comprising a solvent mixture consisting of a high donor number solvent and a moderate donor number solvent, an amount of electrolyte salt and a compatible gelling agent; and
- circuit means configured to apply desired potential differences between the working electrode and the reference electrode, said circuit means further including potential control means to modulate said desired potential differences on a time variable basis and including means to measure cell output based on the oxidation or reduction in ascending potential order of each species of interest.

25. The apparatus of claim 24 further comprising means for supporting said electrodes.

* * * * *